US011948226B2

(12) United States Patent
Balter et al.

(10) Patent No.: US 11,948,226 B2
(45) Date of Patent: Apr. 2, 2024

(54) SYSTEMS AND METHODS FOR CLINICAL WORKSPACE SIMULATION

(71) Applicant: Covidien LP, Mansfield, MA (US)

(72) Inventors: Max L. Balter, Boston, MA (US); Michael A. Eiden, Allston, MA (US); William J. Peine, Ashland, MA (US); Unnas W. Hussain, Albany, NY (US); Justin R. Chen, Morganville, NJ (US)

(73) Assignee: COVIDIEN LP, Mansfield, MA (US)

( * ) Notice: Subject to any disclaimer, the term of this patent is extended or adjusted under 35 U.S.C. 154(b) by 51 days.

(21) Appl. No.: 17/735,604

(22) Filed: May 3, 2022

(65) Prior Publication Data

US 2022/0383555 A1 Dec. 1, 2022

Related U.S. Application Data

(60) Provisional application No. 63/194,211, filed on May 28, 2021.

(51) Int. Cl.
  *G06T 11/00* (2006.01)
  *A61B 90/00* (2016.01)
  *A61B 34/10* (2016.01)

(52) U.S. Cl.
  CPC .............. *G06T 11/00* (2013.01); *A61B 90/37* (2016.02); *A61B 2034/102* (2016.02); *A61B 2034/107* (2016.02); *A61B 2090/365* (2016.02); *G06T 2210/21* (2013.01); *G06T 2210/41* (2013.01)

(58) Field of Classification Search
  CPC . G06T 11/00; G06T 2210/21; G06T 2210/41; A61B 90/37; A61B 2034/102; A61B 2034/107; A61B 2090/365; A61B 34/10; A61B 90/361; A61B 34/30; A61B 2034/101; A61B 2034/108; G16H 30/40; G16H 50/50; G16H 40/60; G06F 3/011
  See application file for complete search history.

(56) References Cited

U.S. PATENT DOCUMENTS

| 6,132,368 | A | 10/2000 | Cooper |
| 6,206,903 | B1 | 3/2001 | Ramans |
| 6,246,200 | B1 | 6/2001 | Blumenkranz et al. |
| 6,312,435 | B1 | 11/2001 | Wallace et al. |

(Continued)

FOREIGN PATENT DOCUMENTS

| EP | 3246135 A1 | 11/2017 |
| WO | 2018032083 A1 | 2/2018 |

(Continued)

OTHER PUBLICATIONS

Extended European Search Report issued in corresponding Application EP 22175900.4 dated Oct. 20, 2022 (8 pages).

*Primary Examiner* — Maurice L. McDowell, Jr.
(74) *Attorney, Agent, or Firm* — Carter, DeLuca & Farrell LLP

(57) ABSTRACT

A computer-implemented method for clinical workspace simulation includes capturing a real-world environment by an imaging device of an augmented reality headset and generating a composite view by rendering a first virtual object relative to a surgical table in the real-world environment. Captured real-world environment and the rendered first virtual object are combined in the composite view, which is displayed on a display of the augmented reality headset worn by a user.

18 Claims, 11 Drawing Sheets

(56) References Cited

U.S. PATENT DOCUMENTS

| | | |
|---|---|---|
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |

(56) References Cited

U.S. PATENT DOCUMENTS

| | | |
|---|---|---|
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |

(56) References Cited

U.S. PATENT DOCUMENTS

| | | |
|---|---|---|
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2007/0293734 A1 * | 12/2007 | Coste-Maniere ...... A61B 34/70 606/1 |
| 2009/0144664 A1 | 6/2009 | Kramer et al. |
| 2015/0130790 A1 * | 5/2015 | Vasquez, II ........... G06T 19/006 345/419 |
| 2017/0312032 A1 * | 11/2017 | Amanatullah .......... G09B 23/30 |
| 2019/0005838 A1 * | 1/2019 | Yu ........................... G06F 3/011 |
| 2019/0209241 A1 * | 7/2019 | Begg .................. A61B 17/3423 |
| 2020/0249654 A1 * | 8/2020 | Edwards .............. G05B 19/414 |
| 2021/0022812 A1 * | 1/2021 | Tako ...................... G16H 20/40 |
| 2021/0121232 A1 * | 4/2021 | Fuerst ................... G16H 20/40 |

FOREIGN PATENT DOCUMENTS

| | | | |
|---|---|---|---|
| WO | 2019006202 A1 | 1/2019 | |
| WO | WO-2019006202 A1 * | 1/2019 | ............ A61B 1/313 |
| WO | 2019139931 A1 | 7/2019 | |
| WO | WO-2019203860 A1 * | 10/2019 | ......... A61B 17/3423 |
| WO | 2020260939 A1 | 12/2020 | |

\* cited by examiner

SYSTEMS AND METHODS FOR CLINICAL WORKSPACE SIMULATION

CROSS-REFERENCE TO RELATED APPLICATION

This application claims the benefit of and priority to U.S. patent Provisional Application No. 63/194,211, filed on May 28, 2021. The entire disclosure of the foregoing application is incorporated by reference herein.

BACKGROUND

Technical Field

The disclosure generally relates to systems and methods for clinical workspace simulations. In particular, the present disclosure is directed to a virtual or augmented reality simulated setup of surgical robotic systems.

Background of Related Art

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a worksite within the patient's body.

Setup time for robotic surgical systems can be lengthy, and may not account for potential collisions between robotic arms during a surgery. Thus, there is a need for systems to determine initial robotic system component placement.

SUMMARY

In accordance with aspects of the disclosure, a computer-implemented method for clinical workspace simulation is presented. The method includes capturing a real-world environment by an imaging device of an augmented reality headset and generating a composite view. The composite view is generated by rendering a first virtual object relative to a surgical table in the real-world environment and combining the captured real-world environment and the rendered first virtual object. The method further includes displaying the composite view on a display of the augmented reality headset.

In an aspect of the disclosure, wherein the method may further include rendering a second virtual object in the composite view and detecting a potential collision with the second virtual object.

In another aspect of the disclosure, the second virtual object may include a virtual robotic arm, the surgical table, a control tower, and/or a console.

In yet another aspect of the disclosure, the method may further include displaying, on the display, an indication to a user providing a suggestion on avoiding the potential collision based on the detection of the potential collision.

In a further aspect of the disclosure, the method may further include detecting a patient in the real-world environment by the imaging device, displaying the detected patient by a display of the augmented reality device, determining a surgical port entry point in an abdominal portion of the displayed patient based on the composite view, and rendering the surgical port entry point in the abdominal portion of the displayed patient.

In yet a further aspect of the disclosure, the method may further include generating an optimized robotic arm placement location based on the surgical port entry point.

In an aspect of the disclosure, the surgical port entry point may be further based on a body habitus of the patient.

In yet a further aspect of the disclosure, the method may further include rendering a visual overlay on the patient and/or the first virtual object.

In another aspect of the disclosure, the method may further include capturing an arm of a user, displaying the arm of the user, detecting a spatial location of the displayed arm of the user, and determining an interaction between the user and the first virtual object.

In yet a further aspect of the disclosure, the method may further include moving the location of the first virtual object in the composite view based on the interaction between the user and the first virtual object.

In accordance with aspects of the disclosure, a system for clinical workspace simulation includes an augmented reality headset including an imaging device configured to capture images of a real-world environment, a display configured to display a composite view, a processor, and a memory. The memory includes instructions stored thereon, which, when executed by the processor, cause the system to capture a real-world environment by the imaging device of the augmented reality headset, generate a composite view by rendering a first virtual object relative to a surgical table in the real-world environment and combining the captured real-world environment and the rendered first virtual object. The instructions, when executed by the processor, further cause the system to display the composite view on the display of the augmented reality headset.

In yet another aspect of the disclosure, the instructions, when executed by the processor, may further cause the system to render a second virtual object in the composite view and detect a potential collision with the second virtual object.

In a further aspect of the disclosure, the second virtual object includes a virtual robotic arm, the surgical table, a control tower, and/or a console.

In yet a further aspect of the disclosure, the instructions, when executed by the processor, may further cause the system to display, on the display, an indication to a user providing a suggestion on avoiding the potential collision based on the detection of the potential collision.

In accordance with aspects of the disclosure, the instructions, when executed by the processor, further may cause the system to detect a patient in the real-world environment by the imaging device, display the detected patient by a display of the augmented reality device, determine a surgical port entry point in an abdominal portion of the displayed patient based on the composite view, and render the surgical port entry point in the abdominal portion of the displayed patient.

In an aspect of the disclosure, the instructions, when executed by the processor, may further cause the system to generate an optimized robotic arm placement location based on the surgical port entry point.

In another aspect of the disclosure, the surgical port entry point may be further based on a body habitus of the patient.

In yet another aspect of the disclosure, the instructions, when executed by the processor, may further cause the system to capture an arm of a user, display the arm of the user, detect a spatial location of the displayed arm of the user, and determine an interaction between the user and the first virtual object.

In a further aspect of the disclosure, the instructions, when executed by the processor, may further cause the system to move the location of the first virtual object in the composite view based on the interaction between the user and the first virtual object and rendering a visual overlay on the patient and/or the virtual object.

In accordance with aspects of the disclosure, a non-transitory computer-readable medium storing instructions which, when executed by a processor, cause the processor to perform a method including capturing a real-world environment by an imaging device of an augmented reality headset; generating a composite view by rendering a virtual robotic arm relative to a surgical table in the real-world environment and combining the captured real-world environment and the rendered virtual robotic arm; and displaying the composite view on a display of the augmented reality headset.

BRIEF DESCRIPTION OF THE DRAWINGS

Various aspects of the disclosure are described herein with reference to the drawings wherein.

DETAILED DESCRIPTION

Figure 1:
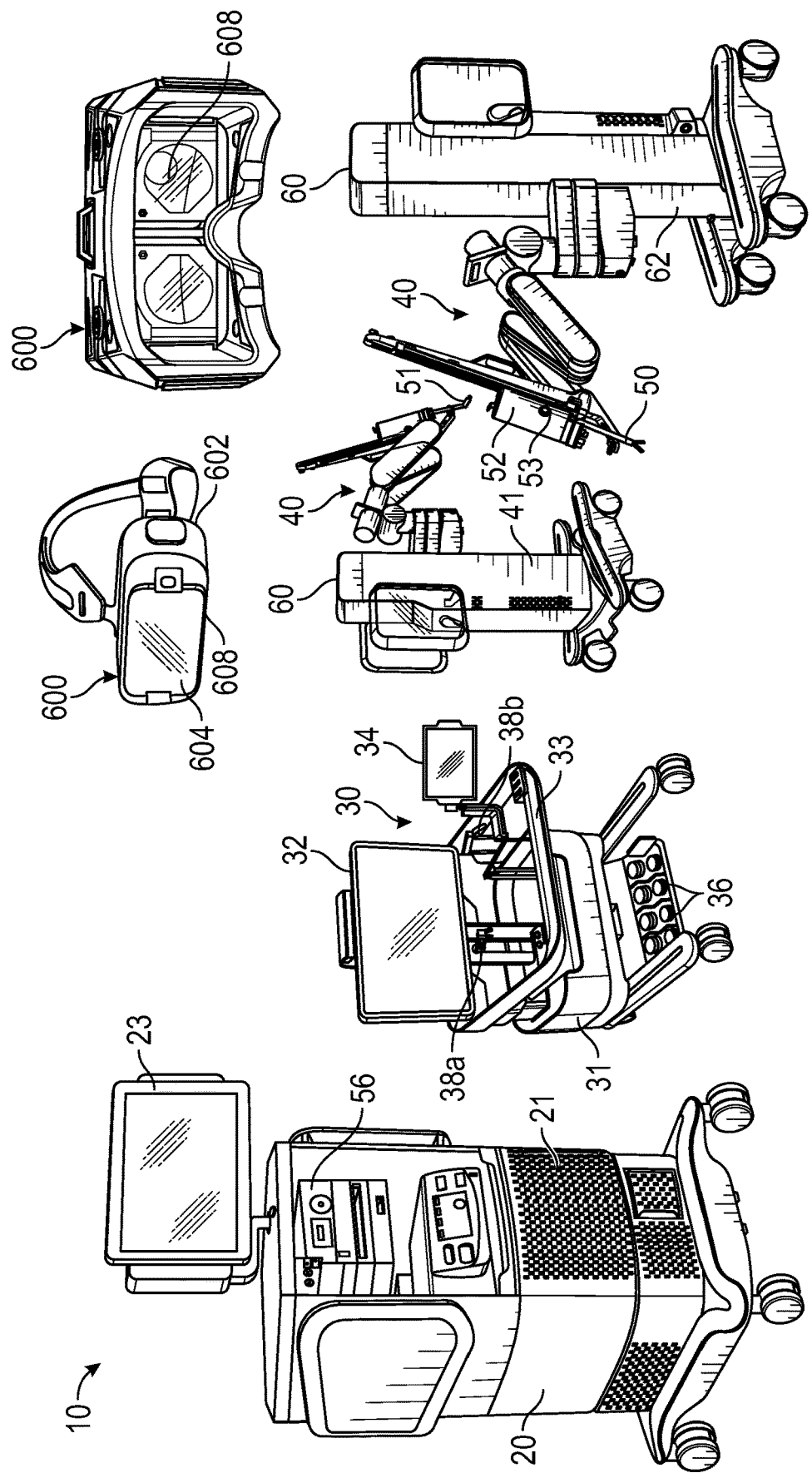
FIG. 1 is a schematic illustration of a surgical robotic system including a control tower, a console, and one or more surgical robotic arms according to an aspect of the disclosure.

Aspects of the presently disclosed surgical robotic system are described in detail with reference to the drawings, in which like reference numerals designate identical or corresponding elements in each of the several views. As used herein, the term "distal" refers to the portion of the surgical robotic system and/or the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller or on a user device, including, for example, a mobile device, a personal computer, or a server system.

As will be described in detail below, the disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 generally includes an augmented reality headset 600, a control tower 20, which is connected to all of the components of the surgical robotic system 10, including a surgical console 30 and one or more robotic arms 40. Each of the robotic arms 40 includes a surgical instrument 50 removably coupled thereto. Each of the robotic arms 40 is also coupled to a movable cart 60.

Figure 7:
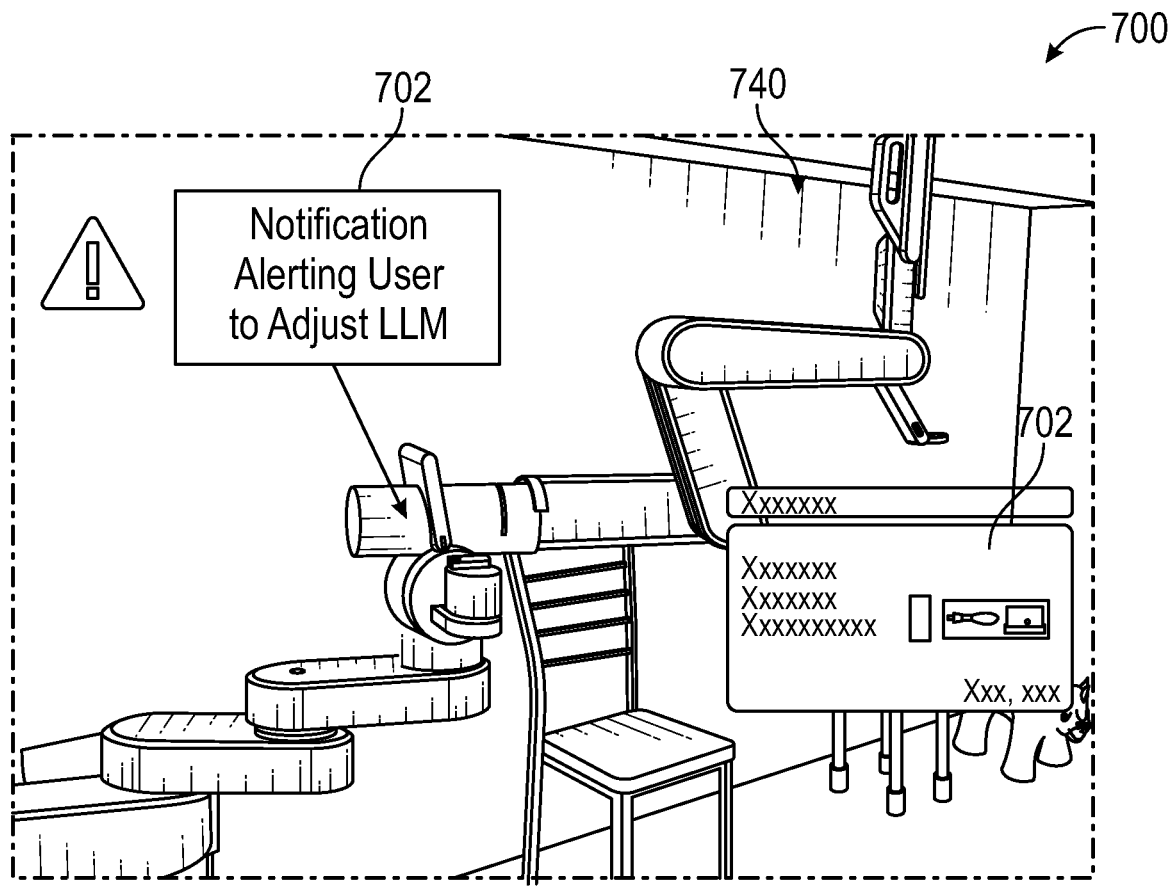
FIG. 7 is an image of a composite view of the clinical workspace simulation with a virtual robotic arm according to an aspect of the disclosure.

The augmented reality headset 600 configured to display a composite view generally includes a controller 602, an imaging device 604, and a display 608. The controller 602 includes a memory configured to have instructions stored thereon and a processor configured to execute the instructions. The augmented reality headset 600 may overlay virtual objects such as a virtual robot arm (FIG. 7). For example, the augmented reality headset 600 can provide users advice on how to position various virtual objects to help set up an operating room for a surgery.

The surgical instrument 50 is configured for use during minimally invasive surgical procedures. In aspects, the surgical instrument 50 may be configured for open surgical procedures. In aspects, the surgical instrument 50 may be an endoscope, such as an endoscopic camera 51, configured to provide a video feed for the user. In further aspects, the surgical instrument 50 may be an electrosurgical forceps configured to seal tissue by compressing tissue between jaw members and applying electrosurgical current thereto. In yet further aspects, the surgical instrument 50 may be a surgical stapler including a pair of jaws configured to grasp and clamp tissue while deploying a plurality of tissue fasteners, e.g., staples, and cutting stapled tissue.

One of the robotic arms 40 may include the endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 perform the image processing based on the depth estimating algorithms of the disclosure and output the processed video stream.

The surgical console 30 includes a first display 32, which displays a video feed of the surgical site provided by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs.

The surgical console 30 also includes a plurality of user interface devices, such as foot pedals 36 and a pair of handle controllers 38a and 38b which are used by a user to remotely control robotic arms 40. The surgical console further includes an armrest 33 used to support clinician's arms while operating the handle controllers 38a and 38b.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38a and 38b.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
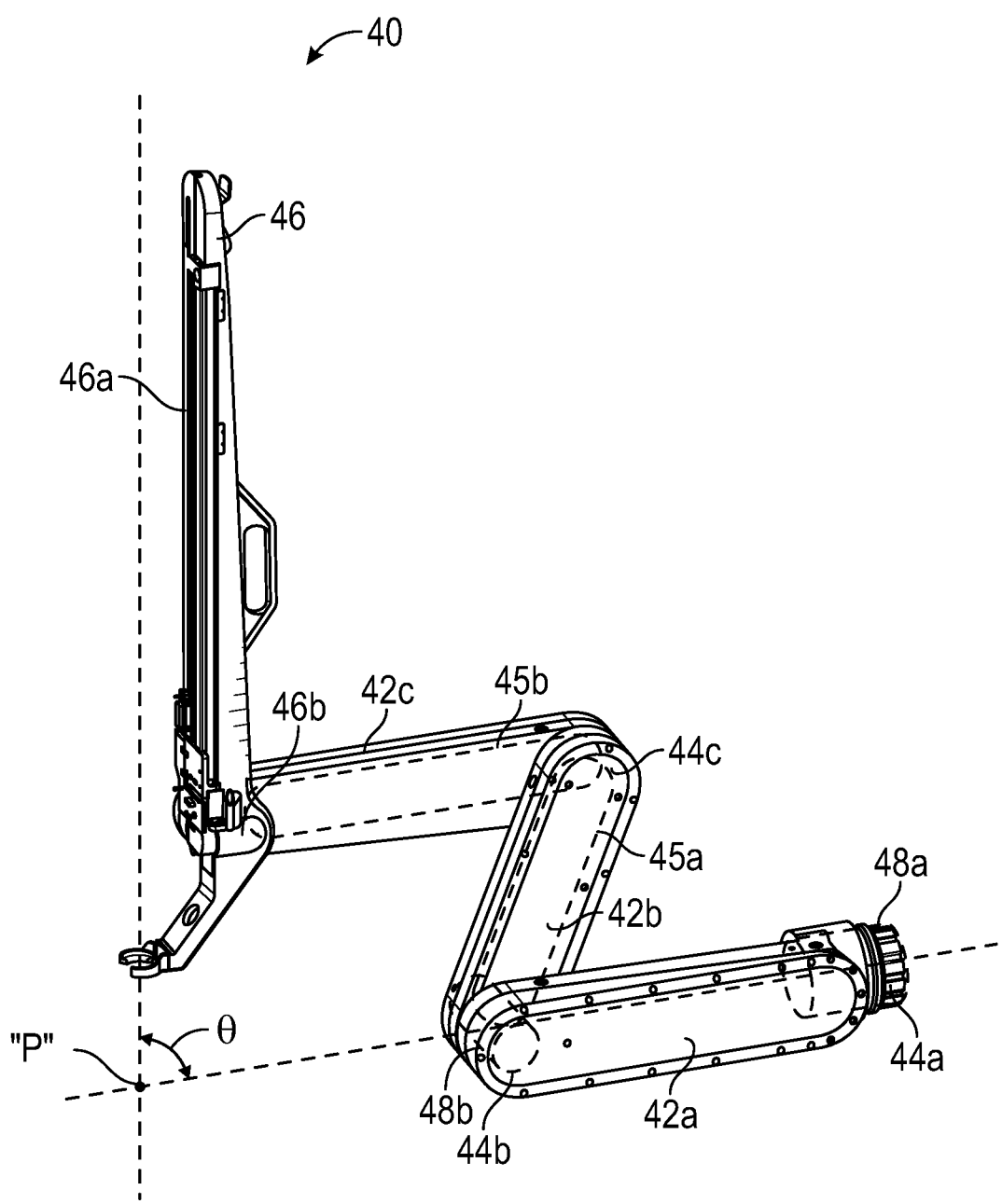
FIG. 2 is a perspective view of a surgical robotic arm of the surgical robotic system of FIG. 1 according to an aspect of the disclosure.
Figure 3:
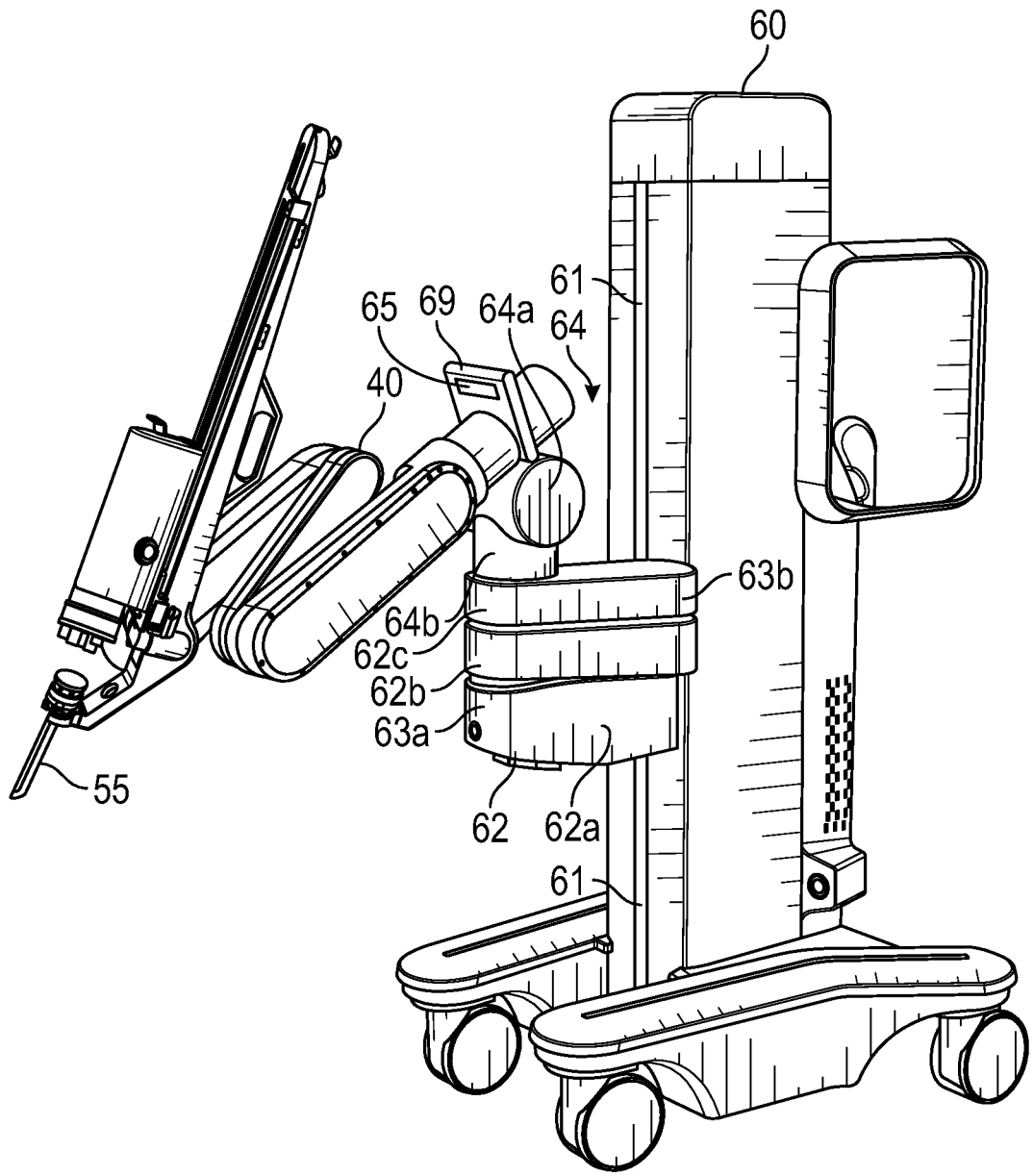
FIG. 3 is a perspective view of a setup arm with the surgical robotic arm of the surgical robotic system of FIG. 1 according to an aspect of the disclosure.

With reference to FIG. 2, each of the robotic arms 40 may include a plurality of links 42a, 42b, 42c, which are interconnected at joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In aspects, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

The actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In aspects, some, or all of the joints 44a, 44b, 44c may include an actuator to obviate the need for mechanical linkages.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

With reference to FIG. 2, the robotic arm 40 also includes a holder 46 defining a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector) of the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c. During endoscopic procedures, the instrument 50 may be inserted through an endoscopic port 55 (FIG. 3) held by the holder 46.

The robotic arm 40 also includes a plurality of manual override buttons 53 (FIGS. 1 and 5) disposed on the IDU 52 and the setup arm 62, which may be used in a manual mode. The user may press one or more of the buttons 53 to move the component associated with the button 53.

Figure 4:
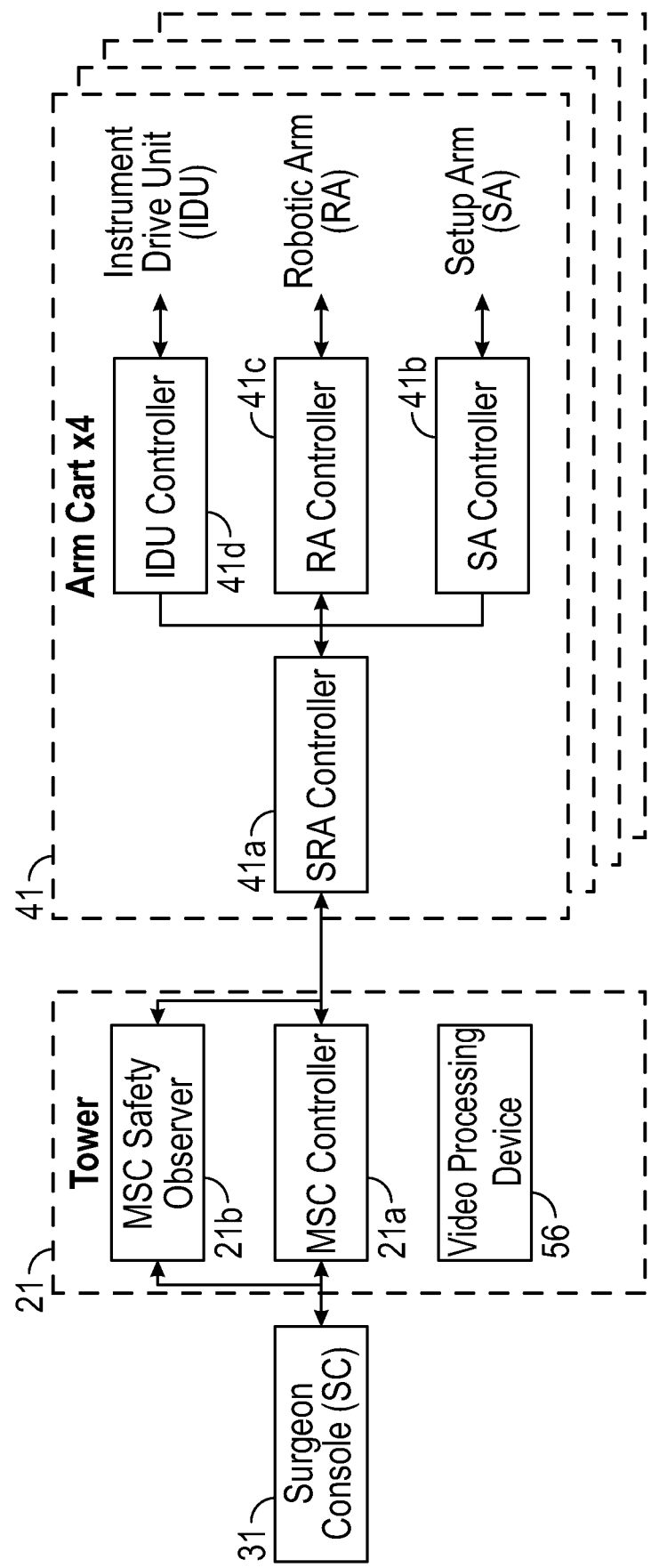
FIG. 4 is a schematic diagram of a computer architecture of the surgical robotic system of FIG. 1 according to an aspect of the disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgical console 30 about the current position and/or orientation of the handle controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives the actual joint angles measured by encoders of the actuators 48a and 48b and uses this information to determine force feedback commands that are transmitted back to the computer 31 of the surgical console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the IDU 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled in response to a pose of the handle controller controlling the robotic arm 40, e.g., the handle controller 38a, which is transformed into a desired pose of the robotic arm 40 through a hand-eye transform function executed by the controller 21a. The hand-eye function, as well as other functions described herein, is/are embodied in software executable by the controller 21a or any other suitable controller described herein. The pose of one of the handle controller 38a may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the handle controller 38a is then scaled by a scaling function executed by the controller 21a. In aspects, the coordinate position is scaled down and the orientation is scaled up by the scaling function. In addition, the controller 21a also executes a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

The video processing device 56 is configured to process the video feed from the endoscope camera 51 and to output a processed video stream on the first displays 32 of the surgical console 30 and/or the display 23 of the control tower 20.

Figure 5:
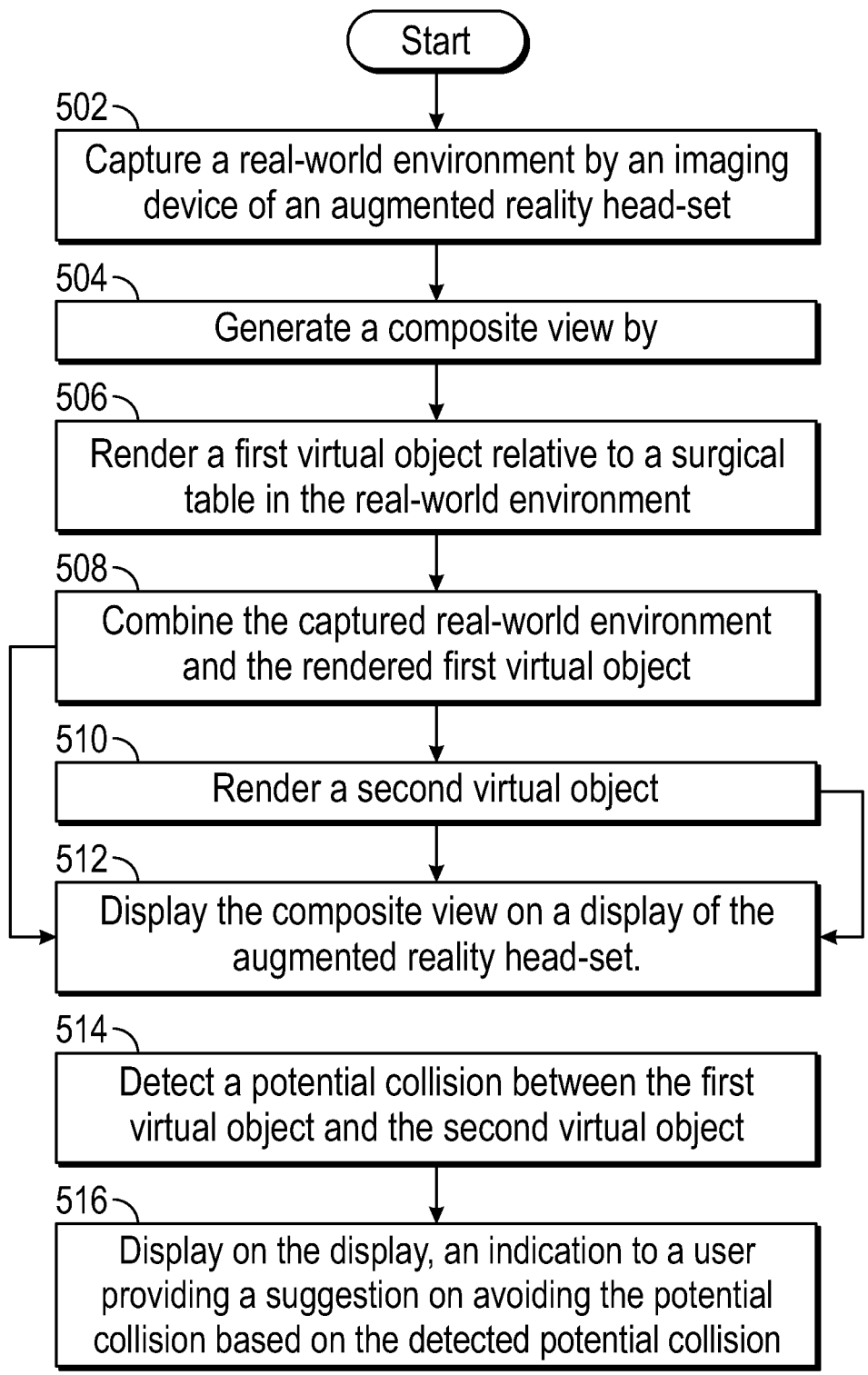
FIG. 5 is a flow chart for a computer-implemented method for clinical workspace simulation according to an aspect of the disclosure.

FIG. 5 shows a flow chart illustrating the various operations of an exemplary method for clinical workspace simulation. Persons skilled in the art will appreciate that one or more operations of the method 500 may be performed in a different order, repeated, and/or omitted without departing from the scope of the disclosure. In various aspects, the illustrated method 500 can operate in controller 602 (FIG. 1), in a remote device, or in another server or system. Other variations are contemplated to be within the scope of the disclosure. The operations of method 500 will be described with respect to a controller, e.g., controller 602 (FIG. 1) of augmented reality headset 600 (FIG. 1), but it will be understood that the illustrated operations are applicable to other systems and components thereof as well.

Initially, at step 502, the controller 602 captures a real-world environment by an imaging device 604 of an augmented reality headset 600 (FIG. 1) (or a mobile device/tablet). The imaging device 604 may include a stereographic imaging device. The controller 602 may generate a 3-D representation of the captured real-world.

Next, at step 504, the controller 602 generates a composite view 700 (FIG. 7). The composite view may include virtual objects 740, 730 overlaid on the real-world environment. The composite view 700 may represent a clinical workspace simulation, which may be used, for example, to guide staff in setting up a surgical robotic system 10.

When generating a composite view, at step 506, the controller 602 renders a first virtual object (e.g., a virtual robot arm, a virtual surgical console 730) relative to a surgical table in the real-world environment. The initial position of the virtual object 740 may be based on, for example, a type of surgical procedure, a patient body habitus, real-world objects in the operating room (e.g., the surgical table and/or clinical staff), and/or a surgical port location. The virtual object 740 may move and function analogously to its real-world counterpart so that a clinician may position and move the virtual object 740 and/or the virtual object's components to determine an initial setup for a surgery.

Figure 8:
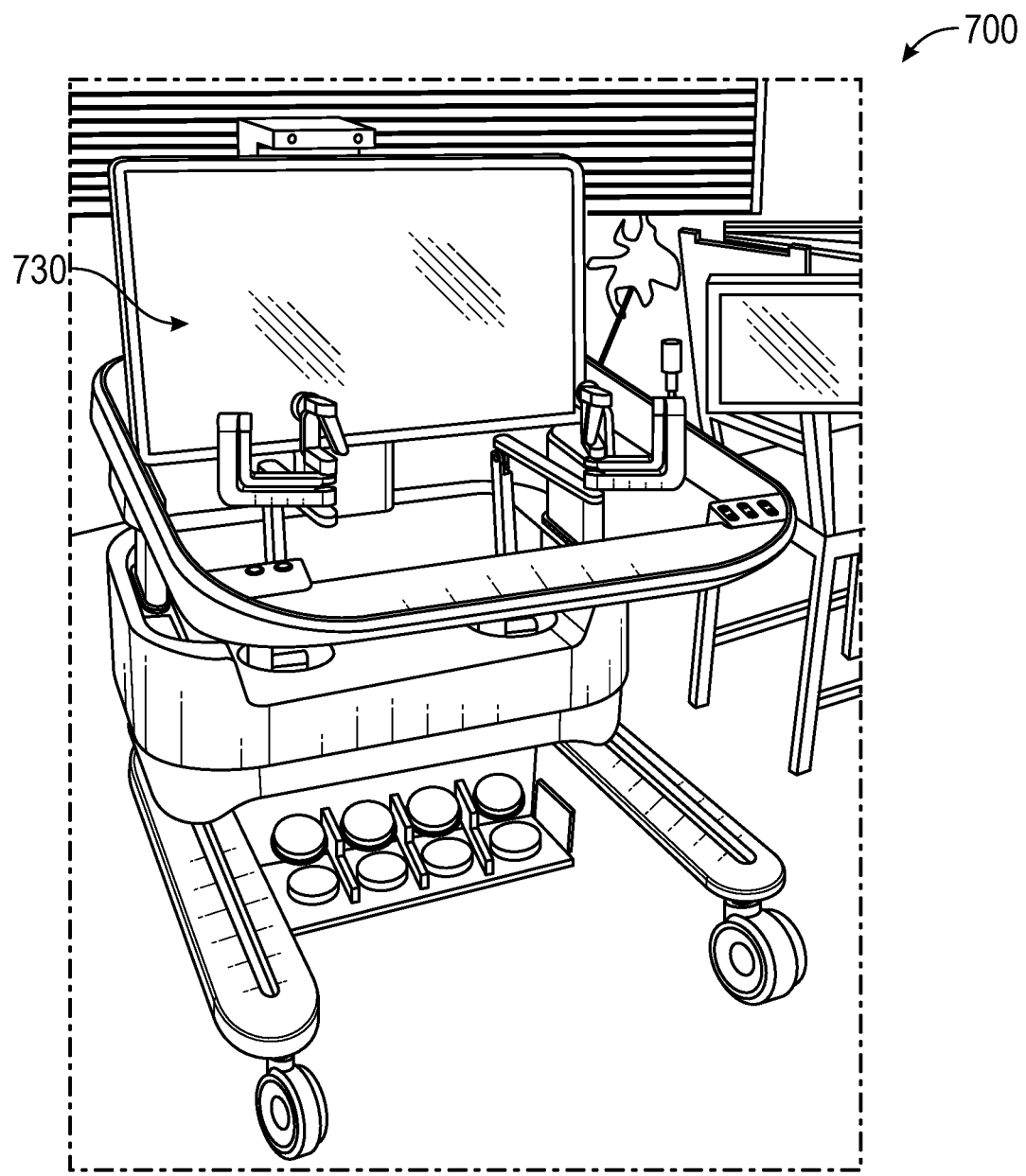
FIG. 8 is an image of a composite view of the clinical workspace simulation with a virtual surgical console according to an aspect of the disclosure.

At step 508, the controller 602 combines the captured real-world environment and the first rendered object, e.g., first virtual robotic arm 740 (FIG. 9) or a virtual surgical console 730. The first rendered object may be displayed in the operating room in the composite view (FIG. 8).

Next, at step 510, the controller 602 renders a second virtual object 740b in the composite view. The second virtual object 740b may include, for example, a robotic arm, the surgical table, a control tower, and/or a surgical console. Although two virtual objects are used in the above example, multiple objects may be rendered.

Figure 11:
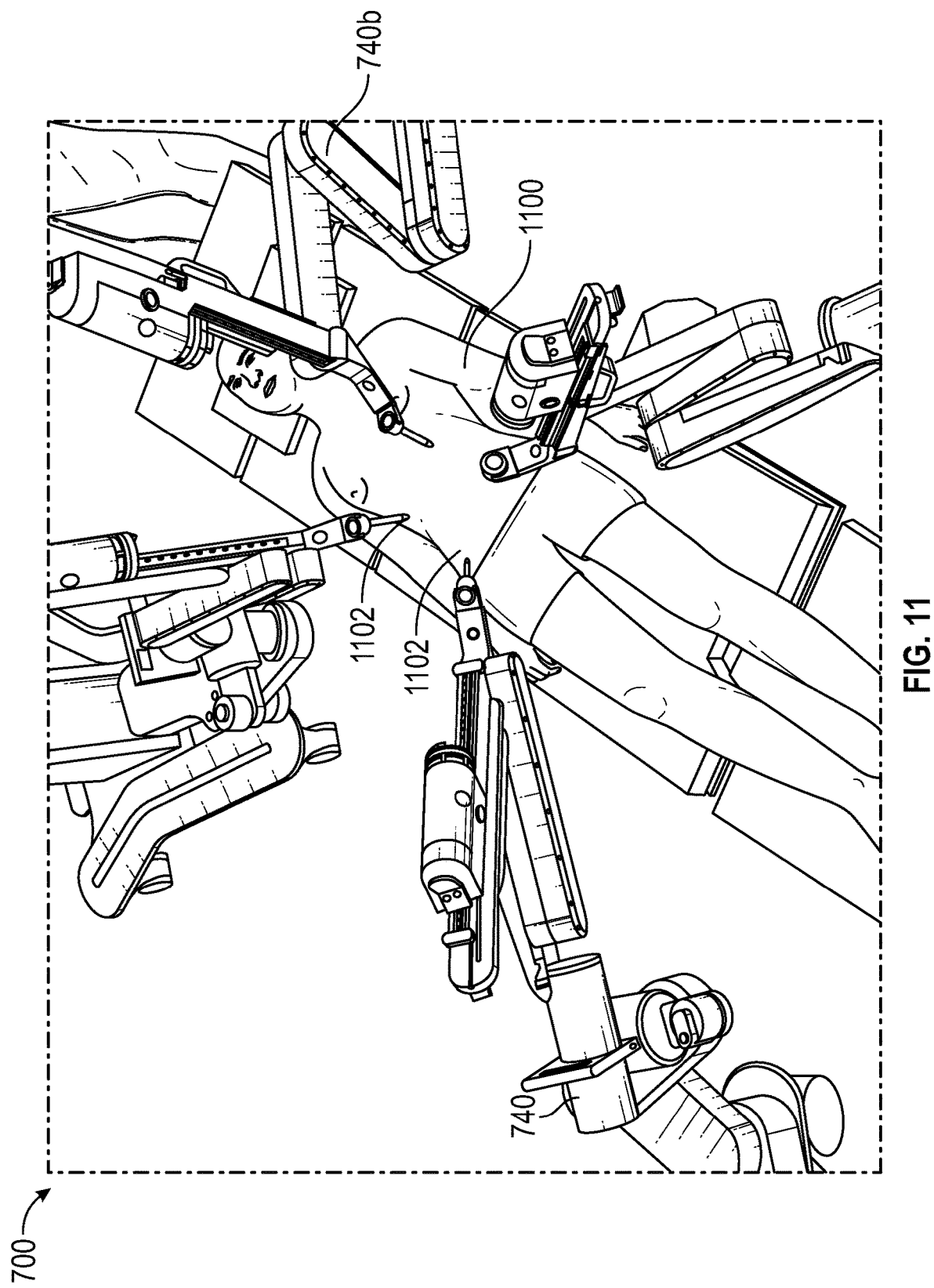
FIG. 11 is an image of the composite view showing virtual robotic arms placed relative to a surgical bed.

Next, at step 512, the controller 602 displays the composite view on a display of the augmented reality headset, which may include a 3-D representation of several virtual robotic arms positioned around a surgical table as shown in FIG. 11. The controller 602 may also suggest optimal placement of these virtual objects 740, 740b based on their function and the type of surgery. In aspects, the controller 602 may display the composite view on a user device, such as a mobile device and/or a tablet.

Next, at step 514, the controller 602 detects a potential collision between virtual objects 740, 740b. The controller 602 may use a bounding volume technique (such as axis-aligned bounding boxes or by bounding spheres) to detect collisions between virtual objects (such as the first and second virtual objects 740, 740b) in the composite view. In aspects, the virtual objects 740, 740b may be assigned 3-D coordinates in the composite view to help with detecting collisions.

Next, at step 516, the controller 602 displays, on the display, an indication to a user providing a suggestion on avoiding the potential collision based on the determined collision. The controller 602 may also display an indication to move the second virtual object 740b a predetermined distance or to the other side of the surgical table.

Figure 6:
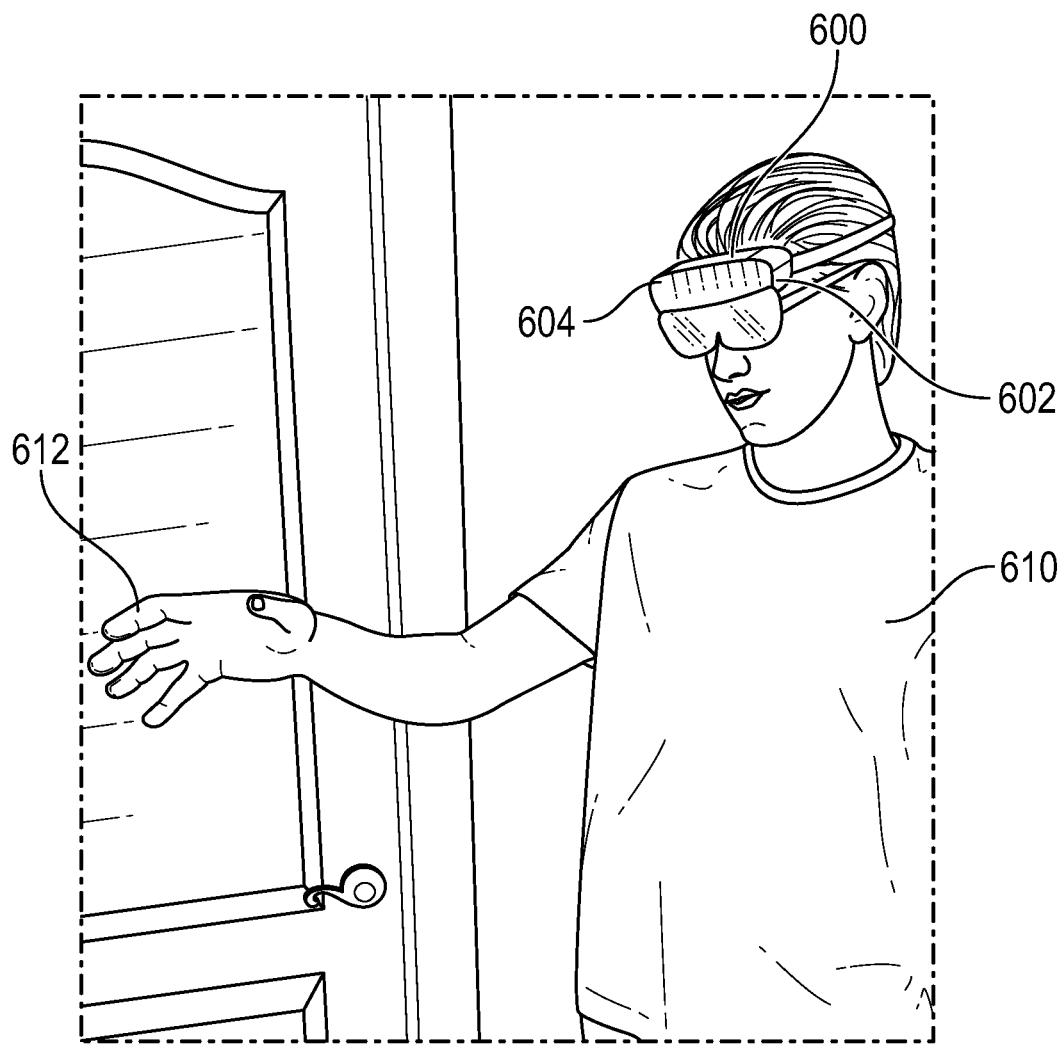
FIG. 6 is a diagram of a user with an augmented reality device of the surgical robotic system of FIG. 1, according to an aspect of the disclosure.
Figure 9:
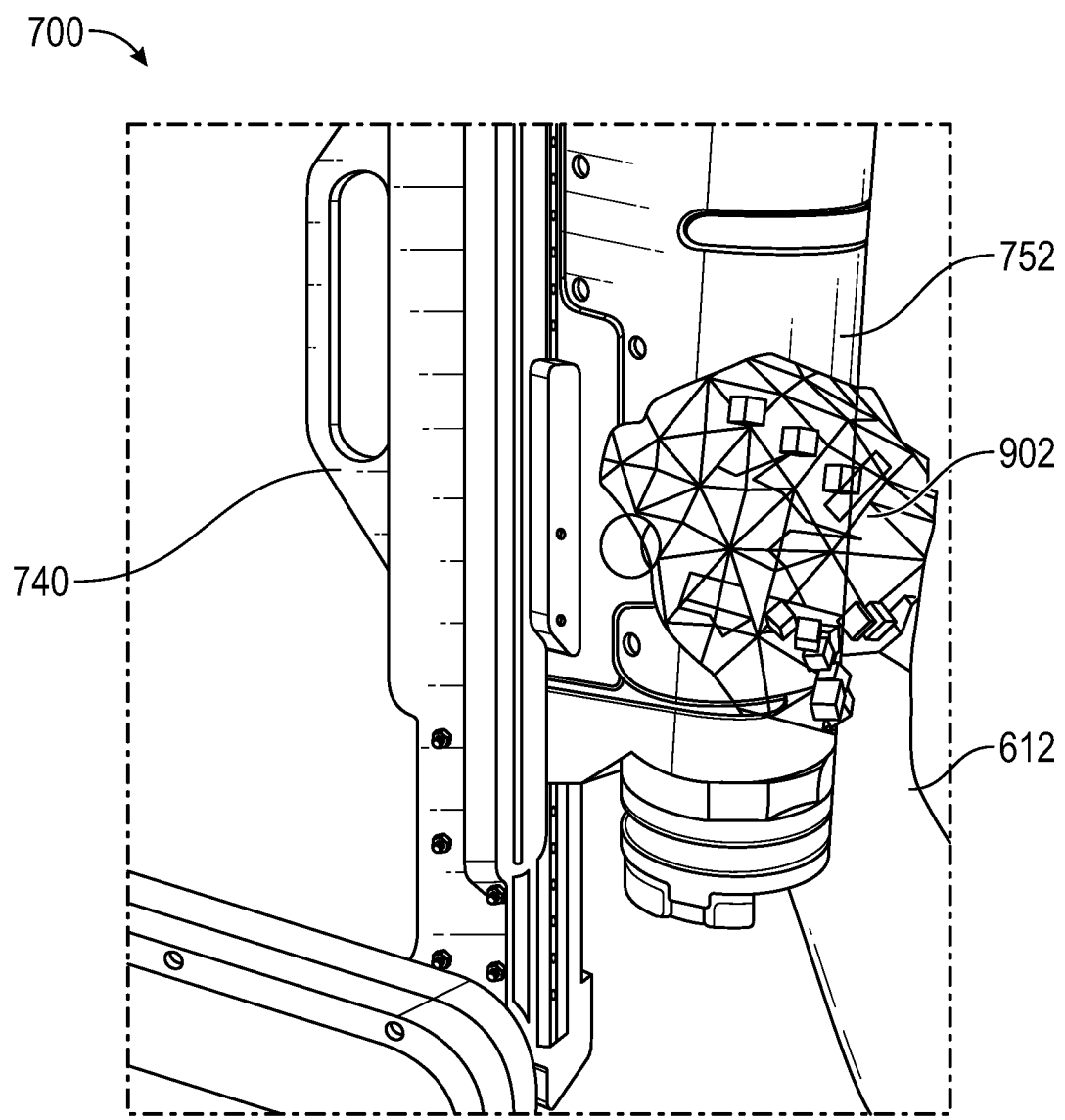
FIGS. 9 and 10 are images of the composite view where the user's hand is interacting with the virtual object, according to an aspect of the disclosure.
Figure 10:
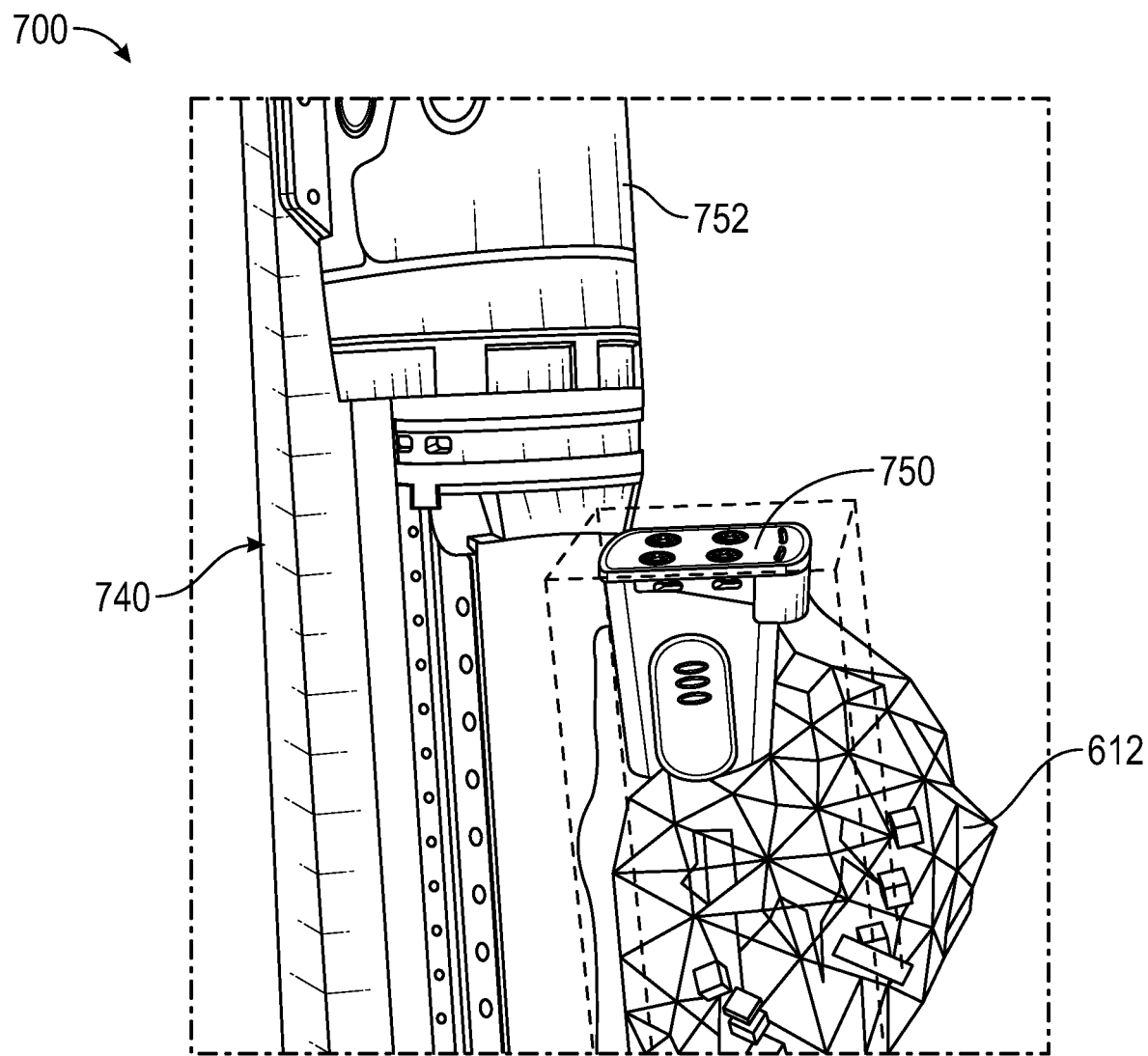

Referring to FIGS. 9 and 10, images of a hand 612 of a user interacting with the virtual object 740 are shown. In aspects, the controller 602 may capture a hand 612 of a user 610 (FIG. 6) and display the hand 902 of the user. The controller 602 may detect a spatial location of the displayed hand 612 of the user 610 and determine an interaction between the user 610 and the first virtual object 740, such as virtual robotic arm. In aspects, the controller 602 may move the location of the first virtual object 740 in the composite view based on the interaction between the user and the first virtual object 740. The virtual robotic arm 740 also includes a virtual instrument drive unit (IDU) 752. The virtual IDU 52 is configured to couple to an actuation mechanism of a virtual surgical instrument 50. Furthermore, the controller 602 enables the user to replace and/or interact with the virtual surgical tool 750.

The controller 602 may provide enhanced feedback to the clinical staff by overlaying information on the composite view, such as recommended surgical port entry points 1102 on the patient's abdomen, and/or the positioning of virtual objects (such as virtual robotic arms (FIG. 7) and virtual surgical console 730 (FIG. 8) around the surgical table). The surgical port entry point 1102 may be based on a body habitus of the patient. In aspects, the controller 602 may render real-time measurements or suggestions of the surgical port entry points 1102 based on the patient body habitus for different locations on the patient. For example, the controller 602 may display an indication 702 (FIG. 7) that the surgical port 1102 should be about 5 cm above and about 5 cm to the left of the naval.

In aspects, the controller 602 may render a visual overlay on the patient and/or the robotic arm. The controller 602 may render a visual overlay such as a possible collision warning and/or a suggested surgical port entry point 1102 placement on a patient 1100 (FIG. 11). In aspects, the controller 602 may detect a patient 1100 (or a clinician) in the real-world environment by the imaging device and display the detected patient by a display 608 (FIG. 1) of the augmented reality headset 600. Real-world objects, such as the patient, the user, and/or the surgical table, may be detected using edge detection and/or image segmentation. The controller 602 may determine a surgical port entry point 1102 (FIG. 11) in an abdominal portion of the displayed patient based on the composite view 700. The controller 602 may render the surgical port entry point 1102 in the abdominal portion of the displayed patient and display the rendered entry point on the display 608. In aspects, the controller 602 may generate an optimized robotic arm placement location (and or orientation) based on the surgical port entry point 1102. The controller 602 may generate an initial virtual robotic arm placement based on the surgical port entry points 1102, then analyze the initial virtual robotic arm placement for possible collisions during surgery. If a potential collision is detected, the controller 602 may provide a series of corrective steps for adjusting placement of the virtual robotic arms 740 which may be displayed on the display. The controller 602 can provide alternative placements of the virtual robotic arms 740 and/or surgical port headset based on the potential collisions. Furthermore, the controller 602 is configured to automatically adjust the position and/or orientation of the surgical port headset and/or virtual robotic arm 740 based on the potential collision. In aspetcs, the controller 602 may overlay patient specific medical imaging, such as images from an MRI and/or a CAT scan. In aspects, the controller may generate an optimized virtual object 740 (e.g., robotic arm) location, orientation, and/or joint angles based on a organ or body part of interest.

In aspects, the controller 602 may provide an alarm (audio and/or visual) if a clinician deviates from normal procedures and may recommend a corrective course of action and how to follow the recommended course of action. In particular, the controller 602 may provide a series of corrective steps, which may be displayed on the display. The controller 602 can provide guidance on how to handle different situations that may block the clinician's progress when setting up and configuring the surgical robotic system 10.

It will be understood that various modifications may be made to the aspects disclosed herein. In aspects, the sensors may be disposed on any suitable portion of the robotic arm. Therefore, the above description should not be construed as limiting but merely as exemplifications of various aspects. Those skilled in the art will envision other modifications within the scope and spirit of the claims appended thereto.

What is claimed is:

1. A computer-implemented method for clinical workspace simulation, the method comprising:
capturing a real-world environment by an imaging device of an augmented reality headset;
detecting a patient in the real-world environment by the imaging device;
generating a composite view by:
rendering a first virtual object relative to a surgical table in the real-world environment; and combining the captured real-world environment and the rendered first virtual object;
determining a surgical port entry point in an abdominal portion of the patient based on the composite view;
rendering the surgical port entry point; and
displaying the composite view including the surgical port entry point in the abdominal portion of the patient on a display of the augmented reality headset.

2. The computer-implemented method of claim 1, further comprising:
rendering a second virtual object in the composite view; and
detecting a potential collision with the second virtual object.

3. The computer-implemented method of claim 2, wherein the second virtual object includes at least one of a virtual robotic arm, the surgical table, a control tower, or a console.

4. The computer-implemented method of claim 2, further comprising:
displaying, on the display, an indication to a user providing a suggestion on avoiding the potential collision based on the detection of the potential collision.

5. The computer-implemented method of claim 1, further comprising:
generating an optimized robotic arm placement location based on the surgical port entry point.

6. The computer-implemented method of claim 1, wherein the surgical port entry point is further based on a body habitus of the patient.

7. The computer-implemented method of claim 1, further comprising:
rendering a visual overlay on at least one of the patient or the first virtual object.

8. The computer-implemented method of claim 1, further comprising:
capturing an arm of a user;
displaying the arm of the user;
detecting a spatial location of the displayed arm of the user; and
determining an interaction between the user and the first virtual object.

9. The computer-implemented method of claim 8, further comprising:
moving the location of the first virtual object in the composite view based on the interaction between the user and the first virtual object.

10. A system for clinical workspace simulation, the system comprising:
an augmented reality headset including:
an imaging device configured to capture images of a real-world environment;
a display configured to display a composite view;
a processor; and
a memory, including instructions stored thereon, which, when executed by the processor, cause the system to:
capture a real-world environment by the imaging device of the augmented reality headset;
detect a patient in the real-world environment by the imaging device generate a composite view by:
rendering a first virtual object relative to a surgical table in the real-world environment; and
combining the captured real-world environment and the rendered first virtual object;
determine a surgical port entry point in an abdominal portion of the patient based on the composite view;
render the surgical port entry point; and
display the composite view on the display of the augmented reality headset.

11. The system of claim 10, wherein the instructions, when executed by the processor, further cause the system to:
render a second virtual object in the composite view; and
detect a potential collision with the second virtual object.

12. The system of claim 11, wherein the second virtual object includes at least one of a virtual robotic arm, the surgical table, a control tower, or a console.

13. The system of claim 11, wherein the instructions, when executed by the processor, further cause the system to:
display, on the display, an indication to a user providing a suggestion on avoiding the potential collision based on the detection of the potential collision.

14. The system of claim 10, wherein the instructions, when executed by the processor, further cause the system to:
generate an optimized object placement location based on the surgical port entry point.

15. The system of claim 10, wherein the surgical port entry point is further based on a body habitus of the patient.

16. The system of claim 10, wherein the instructions, when executed by the processor, further cause the system to:
capture an arm of a user;
display the arm of the user;
detect a spatial location of the displayed arm of the user; and
determine an interaction between the user and the first virtual object.

17. The system of claim 16, wherein the instructions, when executed by the processor, further cause the system to:
move a location of the first virtual object in the composite view based on the interaction between the user and the first virtual object; and
render a visual overlay on at least one of the patient or the virtual object.

18. A non-transitory computer-readable medium storing instructions which, when executed by a processor, cause the processor to perform a method comprising:
capturing a real-world environment by an imaging device;
detecting a patient in the real-world environment by the imaging device;
generating a composite view by:
rendering a virtual robotic arm relative to a surgical table in the real-world environment; and
combining the captured real-world environment and the rendered virtual robotic arm;
determining a surgical port entry point in an abdominal portion of the patient based on the composite view;
rendering the surgical port entry point; and
displaying the composite view including the surgical port entry point in the abdominal portion of the patient on a display.

* * * * *